(12) United States Patent
Mao et al.

(10) Patent No.: US 7,105,500 B2
(45) Date of Patent: Sep. 12, 2006

(54) PROCESS FOR THE ANTIMICROBIAL TREATMENT OF FIBER MATERIALS

(75) Inventors: Jianwen Mao, New Milford, CT (US); Albert Stehlin, Rosenau (FR); Dietmar Ochs, Schopfheim (DE); Victor Paul Eliu, Lörrach (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 10/380,026

(22) PCT Filed: Sep. 6, 2001

(86) PCT No.: PCT/EP01/10283

§ 371 (c)(1),
(2), (4) Date: Mar. 10, 2003

(87) PCT Pub. No.: WO02/22941

PCT Pub. Date: Mar. 21, 2002

(65) Prior Publication Data

US 2005/0080044 A1    Apr. 14, 2005

(30) Foreign Application Priority Data

Sep. 14, 2000  (EP) .................. 00810825
Apr. 30, 2001  (EP) .................. 01810424

(51) Int. Cl.
*A61K 31/724*    (2006.01)
*C08B 30/18*     (2006.01)
*C08B 37/16*     (2006.01)

(52) U.S. Cl. .................. 514/58; 536/103; 536/124

(58) Field of Classification Search .............. 536/1.11, 536/103, 123.1, 124; 514/23, 58, 60, 171
See application file for complete search history.

(56) References Cited

U.S. PATENT DOCUMENTS

| | | | |
|---|---|---|---|
| 4,808,189 A | * | 2/1989 | Oishi et al. ................ 8/408 |
| 5,139,687 A | | 8/1992 | Borgher, Sr. et al. ....... 252/8.6 |
| 5,728,823 A | * | 3/1998 | Reuscher et al. ........... 536/46 |
| 5,874,067 A | * | 2/1999 | Lucas et al. ................ 424/65 |
| 2003/0069453 A1 | | 4/2003 | Fankhauser et al. ....... 568/819 |

FOREIGN PATENT DOCUMENTS

| | | | |
|---|---|---|---|
| DE | 19520967 | | 12/1996 |
| EP | 0306455 | * | 8/1989 |
| EP | 0350147 | | 1/1990 |
| EP | 0908553 | * | 4/1999 |
| WO | 98/17240 | | 4/1998 |
| WO | 00/47811 | | 8/2000 |
| WO | 01/53441 | | 7/2001 |

OTHER PUBLICATIONS

U. Denter et al "Surface Modification Of Synthetic And Natural Fibers By Fixation Of Cyclodextrin Derivatives", Journal of Inclusion Phenomena and Molecular Recogniton in Chemistry, 1996, 25, 197-202.*
McGraw-Hill Dictionary of Scientific and Technical Terms, Third Edition, (1984), p. 1308.
R. T. Morrison et al., Organic Chemistry, Chapter 19, pp. 524-525 and Chapter 20, p. 553.
Denter et al., "Verfahrenstechnische Mothoden Zur Permanent Fixierung Von Cyclodextrinderivaten auf Textilen Oberflaechen" Textilveredlung, CH, Thurgauer Tagblatt, Weinfelden, vol. 32, No. 1/02, (1997), pp. 33-39.
English abstract for DE 19520967 (1996).
U. Denter et al., Journal of Inclusion Phenomena and Molecular Recognition in Chemistry, vol. 25, pp. 197-202, (1996).
H.-J. Buschmann et al., J. Text. Inst., (1998), vol. 89, Part 1, No. 3, pp. 554-561.

* cited by examiner

*Primary Examiner*—Shaojia A. Jiang
*Assistant Examiner*—Ganapathy Krishnan
(74) *Attorney, Agent, or Firm*—Kevin T. Mansfield

(57) ABSTRACT

A process for the antimicrobial treatment of fiber materials, comprising applying to the fiber material an inclusion complex of a fiber-reactive cyclodextrin derivative with an antimicrobial agent selected from the group consisting of (a) halogeno-o-hydroxydiphenyl compounds or non-halogenated hydroxydiphenyl ether compounds; (b) phenol derivatives; (c) benzyl alcohols; (d) chlorohexidine and derivatives thereof; (e) $C_{12-14}$alkybetaines and $C_8$–$C_{18}$fatty acid amidoaklylbetaines; (f) amphoteric surfactants; (g) trihalocarbanilides; (h) quaternary and polyquaternary compounds; and (i) thiazole compounds.

21 Claims, No Drawings

PROCESS FOR THE ANTIMICROBIAL TREATMENT OF FIBER MATERIALS

The present invention relates to a process for the treatment of fiber materials with an inclusion complex of fiber-reactive cyclodextrin derivatives with special antimicrobial agents, aqueous compositions comprising these inclusion complexes, and novel inclusion complexes.

The use of antimicrobials in various textile related applications is increasingly important. Some antimicrobial substances do not have good substantivity to textile substrates, for example cotton. It is often found that when applied to textile materials the antimicrobial agent will be washed off after a few laundering cycles and the antimicrobial activity becomes diminished. Therefore, finding a process or formulation that could prolong the washing durability is scientifically interesting and commercially promising. Surprisingly, it was found that special antimicrobials can be complexed with fiber-reactive cyclodextrin derivatives. The latter is characterized by the presence of a cavity formed by its special molecular configuration. Furthermore, such fiber-reactive cyclodextrin derivatives can be covalently fixed to cotton substrates. Therefore, a controlled delivery system can be made whereby the reactive cyclodextrin acts as both an anchor to the fiber materials as well as a carrier for interested antimicrobial substance.

It was found that the antimicrobial/cyclodextrin complexes, when incorporated to fiber materials, can provide prolonged washing durability. The prolonged presence of antimicrobials incorporated on fiber materials makes the substrates more hygienic, less prone to cross contamination and fresher. The latter aspect is achieved because the selected antimicrobials are able to inhibit the growth of certain microorganisms, especially gram positive bacteria, which are considered as being capable to develop odour by metabolizing certain components in sweat as well other substances that can be found on textile substrates.

Another important aspect is that the performance in inhibiting the formation of odour by the presence of antimicrobials can be enhanced with such a complex. Because cyclodextrin itself has certain capacities in absorbing small odour causing molecules. Therefore, the complex, when incorporated onto the fiber materials, is able to inhibit the odour formation due to bacteria metabolism, as well as absorb other odours available in the environment where textile products are used, such as smoke odour.

Furthermore, due to the change of physical properties of the complex, in comparison to those of the antimicrobials alone, the substantivity of antimicrobials to various textile substrates can be enhanced. Such an aspect is of interest if antimicrobials are used in laundering processes. Conventionally antimicrobials are incorporated into laundry detergent and used in laundering process. But due to poor substantivity of selected antimicrobials towards the substrate, a large portion of the antimicrobials can not be absorbed by the substrate and is washed off together with the laundry liquor. The improvement of the antimicrobial in a carrier system can therefore be benefitial in the following aspects: more efficient use of antimicrobial, less antimicrobial in the effluent and therefore less ecotoxological impact, better stability and less interactions of the antimicrobials with other agents found in common laundry detergent.

The present invention, therefore, relates to a process for the antimicrobial treatment of fiber materials, comprising applying to the fiber material an inclusion complex of a fiber-reactive cyclodextrin derivative with an antimicrobial agent selected from the group consisting of (a) halogen-o-hydroxydiphenyl compounds or non-halogenated hydroxydiphenyl ether compounds;
(b) phenol derivatives;
(c) benzyl alcohols;
(d) chlorohexidine and derivatives thereof;
(e) $C_{12}$–$C_{14}$alkylbetaines and $C_8$–$C_{18}$fatty acid amidoalkylbetaines;
(f) amphoteric surfactants;
(g) trihalocarbanilides;
(h) quaternary and polyquaternary compounds; and
(i) thiazole compounds.

Preferably, the antimicrobial agent (a) as a halogen-o-hydroxydiphenyl compound is selected from compounds of the formula

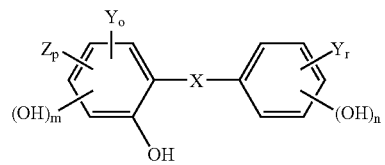

(1)

wherein
X is oxygen, sulfur or —$CH_2$—,
Y is chloro or bromo,
Z is $SO_2H$, $NO_2$ or $C_1$–$C_4$-Alkyl,
r is 0 to 3,
o is 0 to 3,
p is 0 or 1,
m is 0 or 1 and
n is 0 or 1;
and at least one of r or o is ≠0.

Preferably, in the present process, antimicrobial agents (a) of formula (1) are used, wherein
X is oxygen, sulfur or —$CH_2$—, and
Y is chloro or bromo,
m is 0,
n is 0 or 1,
o is 1 or 2,
r is 1 or 2 and
p is 0.

Of particular interest as antimicrobial agent (a) of formula (1) is a compound of formula

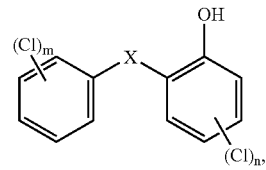

(2)

wherein
X is —O— or —$CH_2$—;
m is 1 to 3; and
n is 1 or 2, and most preferably a compound of formula

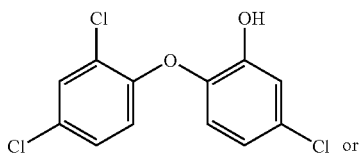

(3)

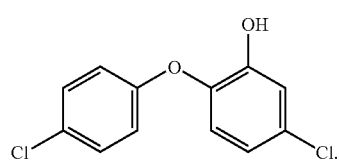

(4)

Preferably, the antimicrobial agent (a) as a non-halogenated hydroxydiphenyl ether compound is selected from compounds of the formula

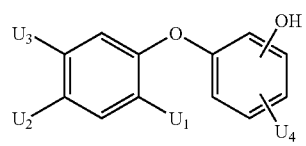

(1')

wherein
$U_1$ and $U_2$ are independently of each other hydrogen, hydroxy, unsubstituted or hydroxy-substituted $C_1$–$C_{20}$alkyl, $C_5$–$C_7$cycloalkyl, $C_1$–$C_6$alkylcarbonyl, $C_1$–$C_{20}$alkoxy, phenyl or phenyl-$C_1$–$C_3$-alkyl;
$U_3$ is hydrogen, $C_1$–$C_{20}$alkyl, $C_1$–$C_{20}$alkoxy or $C_1$–$C_6$alkylcarbonyl; and
$U_4$ is hydrogen, unsubstituted or hydroxy-substituted $C_1$–$C_{20}$alkyl, $C_5$–$C_7$cycloalkyl, hydroxy, formyl, acetonyl, $C_1$–$C_6$alkylcarbonyl, $C_2$–$C_{20}$alkenyl, carboxy, carboxy$C_1$–$C_3$alkyl, $C_1$–$C_3$alkylcarbonyl $C_1$–$C_3$alkyl or carboxyallyl.

$U_1$, $U_2$, $U_3$ and $U_4$ as $C_1$–$C_{20}$alkyl are straight-chain or branched alkyl radicals such as methyl, ethyl, n-propyl, isopropyl, n-butyl, sec-butyl, tert-butyl, pentyl, iso-pentyl, tert-pentyl, hexyl, cyclohexyl, heptyl, octyl, isooctyl, nonyl or decyl and the like.

$U_1$, $U_2$ and $U_3$ as $C_1$–$C_{20}$alkoxy are straight-chain or branched alkoxy radicals such as methoxy, ethoxy, n-propoxy, isopropoxy, n-butoxy, sec-butoxy, tert-butoxy, pentyloxy, iso-pentyloxy, tert-pentyloxy, heptyloxy, octyloxy, isooctyloxy, nonyloxy or decyloxy and the like.

$U_1$, $U_2$, $U_3$ and $U_4$ as $C_1$–$C_6$alkylcarbonyl are straight-chain or branched carbonyl radicals such as acetyl, propionyl, butyryl, isobutyryl, valeryl, isovaleryl or pivaloyl and the like.

$U_1$, $U_2$ and $U_4$ as hydroxy-substituted $C_1$–$C_{20}$alkyl are, for example, hydroxymethyl, hydroxyethyl, hydroxypropyl, hydroxybutyl, hydroxypentyl, hydroxyhexyl, hydroxyheptyl, hydroxyoctyl, hydroxynonyl or hydroxydecyl and the like.

Preferably compounds of formula (1') are used, wherein OH is in the para position with respect to the ether linkage.

$U_1$ and $U_2$ are independently of each other preferably hydrogen, $C_1$–$C_{20}$alkyl, $C_1$–$C_6$ alkylcarbonyl or $C_1$–$C_{20}$alkoxy.

$U_3$ is preferably hydrogen, $C_1$–$C_{20}$alkyl or $C_1$–$C_{20}$alkoxy.

$U_4$ is preferably hydrogen, $C_1$–$C_{20}$alkyl, hydroxy, formyl, acetonyl, allyl, carboxymethyl, carboxyallyl, hydroxy substituted $C_1$–$C_{20}$alkyl or $C_1$–$C_6$ alkylcarbonyl.

Preferred are compounds of formula (1') wherein $U_1$ and $U_3$ are $C_1$–$C_4$alkyl and $U_2$ and $U_4$ are hydrogen.

Compounds of formula (1') which are of particular interest include the following:

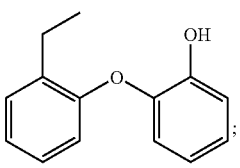 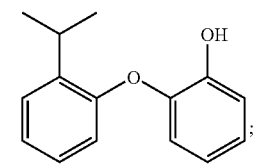

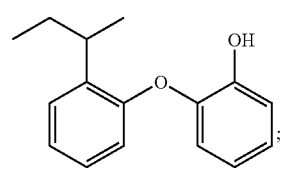 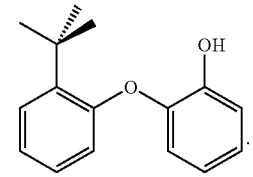

Other compounds of formula (1') which are of particular interest include the following:

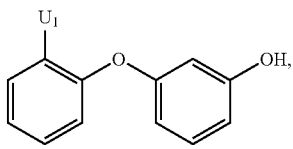

wherein
$U_1$ is $C_1$–$C_5$alkyl; for example the compound of formula

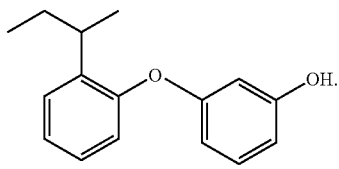

Of interest are also compounds of formula

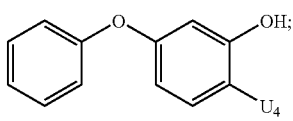

wherein

U₄ is $C_1$–$C_5$alkyl, for example the compound of formula

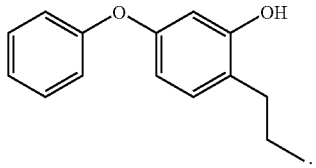

Compounds of particular interest include the following:

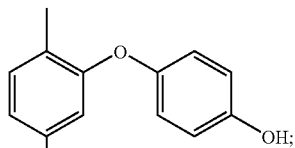

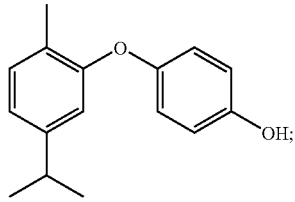

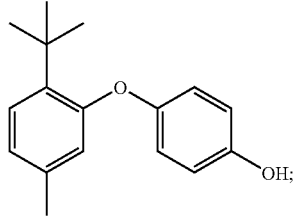

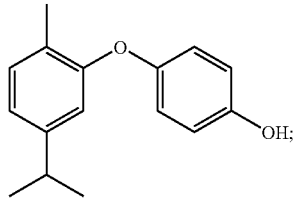

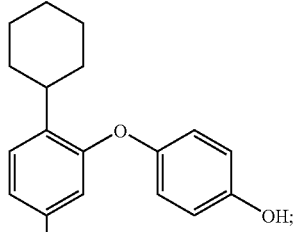

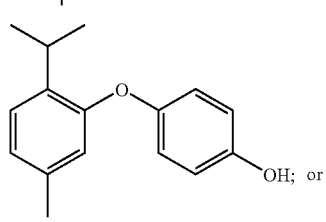

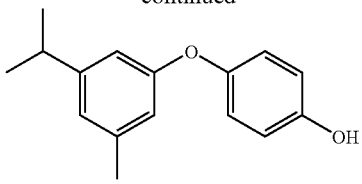

The compounds of formula (1') are known or can be prepared in analogy to known compounds.

Preferred phenol derivatives (b) correspond to formula

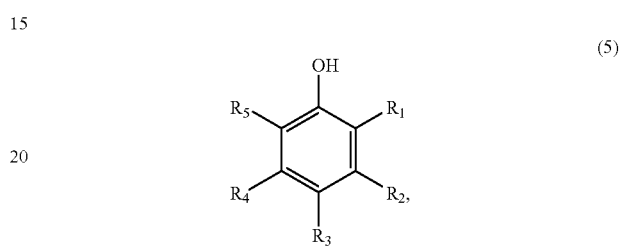

wherein $R_1$ is hydrogen, hydroxy, $C_1$–$C_4$alkyl, chloro, nitro, phenyl or benzyl, $R_2$ is hydrogen, hydroxy, $C_1$–$C_6$alkyl or halogen, $R_3$ is hydrogen, $C_1$–$C_6$alkyl, hydroxy, chloro, nitro or a sulfo group in the form of the alkali metal salts or ammonium salts thereof, $R_4$ is hydrogen or methyl, and $R_5$ is hydrogen or nitro.

Such compounds are typically chlorophenols (o-, m-, p-chlorophenols), 2,4-dichlorophenol, p-nitrophenol, picric acid, xylenol, p-chloro-m-xylenol, cresols (o-, m-, p-cresols), p-chloro-m-cresol, pyrocatechin, resorcinol, orcinol, 4-n-hexylresorcinol, pyrogallol, phloroglucine, carvacrol, thymol, p-chlorothymol, o-phenylphenol, o-benzylphenol, p-chloro-o-benzylphenol, 4-phenolsulfonic acid, hydroxy biphenyls and its salts.

Typical antimicrobial agents (c) correspond to the formula

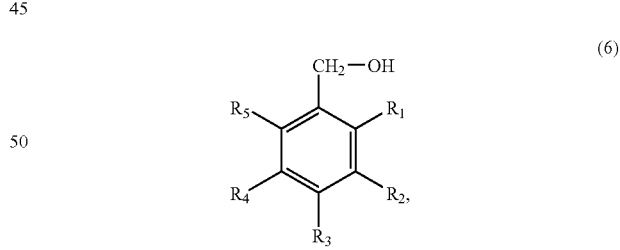

wherein $R_1$, $R_2$, $R_3$, $R_4$ and $R_5$ are each independently of one another hydrogen or chloro.

Illustrative examples of compounds of formula (6) are benzyl alcohol, 2,4-, 3,5- or 2,6-dichlorobenzyl alcohol and trichlorobenzyl alcohol.

Antimicrobial agent (d) is typically chlorhexidine and salts thereof, for example 1,1'-hexamethylene-bis-(5-(p-chlorophenyl)-biguanide), together with organic and inorganic acids and chlorhexidine derivatives such as their diacetate, digluconate or dihydrochloride compounds.

Antimicrobial agent (e) is typically $C_8$–$C_{18}$cocamidopropylbetaine.

Amphoteric surfactants as antimicrobial agents (f) are suitably $C_{12}$alkylaminocarboxylic and $C_1$–$C_3$alkanecarboxylic acids such as alkylaminoacetates or alkylaminopropionates.

Typical trihalocarbanilides which are useful as antimicrobial agent (g) are compounds of the formula

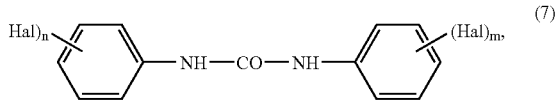

(7)

wherein
Hal is chloro or bromo,
n and m are 1 or 2, and
n+m are 3.

The quaternary and polyquaternary compounds which correspond to antimicrobial agent (h) are typically of the formula

(8)

wherein
$R_6$, $R_7$, $R_8$ and $R_9$ are each independently of one another $C_1$–$C_{18}$alkyl, $C_1$–$C_{18}$alkoxy or phenyl-lower alkyl, and
Hal is chloro or bromo.

Among these salts, the compound of formula

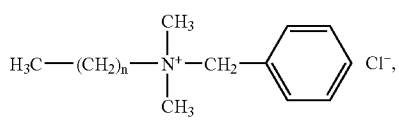

(9)

wherein
n is an integer from 7 to 17, is very particularly preferred.

A further exemplified compound is cetyl trimethylethyl ammonium bromide or poly-(hexamethylene biguanide) hydrochloride.

Antimicrobial agents (i) are typically methylchloroisothiazolone, methylisothiazolone, octylisothiazolone and benzylisothiazolone. Of particular interest as antimicrobial agent (i) is methylchloroisothiazoline.

Further examples of useful antimicrobial agents are zinc pyrithion, propyl paraben, butyl paraben, imidazolidinyl urea, 2-phenoxy ethanol (phenoxyethanol), 1,3-bis(hydroxymethyl)-5,5-dimethyl-2,4-imidazolidinedione (DMDM hydantoin) and 3-iodo-2-propynyl butylcarbamate.

Highly preferred are antimicrobial agents (a).

Fiber-reactive groups of the cyclodextrin derivatives are groups capable of reacting with the fiber material, for example with the hydroxyl groups of cellulose, the amino, carboxyl, hydroxyl or thiol groups in the case of wool and silk or with the amino and possibly carboxyl groups of synthetic polyamides with the formation of covalent chemical bonds. Fiber-reactive groups are generally attached directly or via a bridge member to a carbon atom of the cyclodextrin derivative. Examples of suitable fiber-reactive groups include those which contain at least one detachable substituent on an aliphatic, aromatic or preferably on a heterocyclic radical or in which the radicals mentioned contain a radical suitable for reaction with the fiber material. Examples of suitable bridge members according to which the fiber-reactive groups can be attached to a carbon atom of the cyclodextrin derivative are —O—CO— and preferably —O—.

Examples of fiber-reactive groups include fiber-reactive radicals containing carbo- or heterocyclic 4-, 5- or 6-rings substituted by a detachable atom or group. Examples of heterocyclic radicals include heterocyclic radicals which contain at least one detachable substituent attached to a heterocyclic ring; and those which contain at least one reactive substituent attached to a 5- or 6-membered heterocyclic ring, as to a triazine, pyridine or pyrimidine. The heterocyclic fiber-reactive radicals mentioned may further contain, via a direct bond or via a bridge member, further fiber-reactive radicals.

The fiber-reactive group of the cyclodextrin derivative is preferably a nitrogen-containing heterocycle having at least one substituent selected from the group consisting of halogen, especially fluorine or chlorine, and unsubstituted or substituted pyridinium.

Examples of such fiber-reactive groups are
a) a triazine group of formula

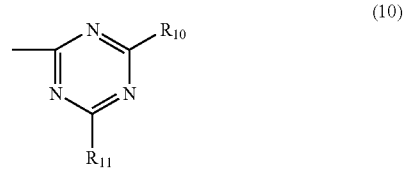

(10)

wherein
$R_{10}$ is fluorine, chlorine or unsubstituted or carboxy-substituted pyridinium, and
$R_{11}$ is as defined above for $R_{10}$ or is a radical of formula —$OR_{12}$ or —$N(R_{13})R_{14}$, wherein
$R_{12}$ is hydrogen, alkali, $C_1$–$C_8$alkyl which is unsubstituted or substituted by hydroxy or $C_1$–$C_4$alkoxy, and
$R_{13}$ and $R_{14}$, independently from each other, are hydrogen; $C_1$–$C_8$alkyl which is unsubstituted or substituted by $C_1$–$C_4$alkoxy, hydroxy, sulfo, sulfato or carboxy; or phenyl which is unsubstituted or substituted by $C_1$–$C_4$alkyl, $C_1$–$C_4$alkoxy, halogen, nitro, carboxy or sulfo;
b) or a pyrimidinyl group of formula

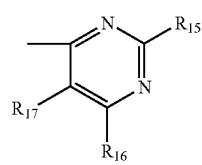

(11)

wherein
one of radicals $R_{15}$ and $R_{16}$ is fluorine or chlorine and the other one of radicals $R_{15}$ and $R_{16}$ is fluorine, chlorine, or is a radical of formula —$OR_{12}$ or —$N(R_{13})R_{14}$ as defined above, and $R_{17}$ is $C_1$–$C_4$alkylsulfonyl, $C_1$–$C_4$alkoxysulfonyl, $C_1$–$C_4$alkoxycarbonyl, $C_2$–$C_4$alkanoyl, chlorine, nitro, cyano, carboxyl or hydroxyl;

c) or a dichloroquinoxaline group of formula

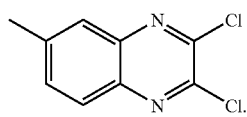 (12)

Highly preferred are groups of formula (10), especially those wherein $R_{10}$ is chlorine.

$R_{11}$ is preferably a radical of formula —$OR_{12}$, wherein $R_{12}$ is hydrogen, alkali or $C_1$–$C_8$alkyl. Preferred radicals $R_{11}$ are those of formula —$OR_{12}$ wherein $R_{12}$ is hydrogen, alkali or $C_1$–$C_4$alkyl, especially hydrogen or alkali. Alkali is highly preferred. Alkali is preferably sodium.

The cyclodextrin derivatives contain preferably 2 to 3 fiber-reactive groups.

Fiber-reactive cyclodextrine derivatives are known and the preparation of such fiber-reactive cyclodextrine derivatives can be carried out according to known processes (see for example U.S. Pat. No. 5,728,823).

For example, trichlorotriazine or trifluortriazine is subjected to a condensation reaction with a compound of formula H—$R_{10}$ and/or H—$R_{11}$ and the resulting fiber-reactive group containing at least one chlorine or fluorine substituent is subjected to a further condensation reaction with the cyclodextrin derivative. The condensation reactions can be carried out at a temperature of 0 to 25° C. in aqueous medium. It is preferred to carry out the condensation reactions under pH-control in slightly alkaline medium.

Preferred as cyclodextrin is β-cyclodextrin.

The preparation of the inclusion complex can be carried out according to known methods. For example, the inclusion complexes can be prepared by combining a mixture A) containing the fiber-reactive cyclodextrin and water with a mixture B) containing the antimicrobial agent and an organic solvent. It is preferred to add either mixture A) or mixture B) in portions. The addition can be carried out at room temperature. The weight ratio of cyclodextrin/water in mixture A) is usually 0.1/1 to 1/0.1, especially 0.5/1 to 1/0.5. A weight ratio of about 1/1 is preferred for mixture A). The weight ratio of antimicrobial agent/organic solvent in mixture B) is usually 0.1/1 to 1/0.1, especially 0.5/1 to 1/0.5. A weight ratio of about 1/1 is preferred for mixture B). The amounts of mixtures A) and B) to be combined can be chosen so that the molar ratio of antimicrobial agent/cyclodextrin is usually 0.1/1 to 1/0.1, especially 0.5/1 to 1/0.5. A molar ratio of about 1/1 is preferred. Preferred organic solvents are methanol and especially ethanol. The preparation of the inclusion complex is carried out, for example, at a pH of ≧7, preferably of ≧9 and especially of ≧10. As the upper limit a pH, for example, of 12 is appropriate.

During and after combination of mixtures A) and B) the resulting mixture is stirred or, if necessary, kneaded, for example for 1 to 24 hours. Then the solvents are removed, for example by drying, at a temperature of 40 to 100° C.

Usually preparations of fiber-reactive inclusion complexes are carried out by first preparing the fiber-reactive cyclodextrin and then introducing the agent to be complexed. However, such a procedure has the disadvantage that the fiber-reactive group is present in all reaction steps and therefore hydrolisation of the fiber-reactive group can take place to a greater extent. Furthermore, it is common practice that the uncomplexed fiber-reactive cyclodextrin is dried after preparation and is dissolved again in water for preparation of the inclusion complex. Such a procedure has the disadvantage that again hydrolisation of the fiber-reactive group can take place during the additional drying step.

It has now been found that hydrolisation can be minimised if a process is used which comprises a) forming an inclusion complex of cyclodextrin with at least one of the antimicrobial agents given before; and then b) introducing at least one fiber-reactive group into the inclusion complex obtained according to step a).

Preferably, the inclusion complex obtained according to step a) is processed directly without intermediate drying.

Step a) is usually carried out at temperatures of 20 to 80° C., especially 40 to 70° C., in an aqueous medium containing the non-reactive cyclodextrin and the antimicrobial agent. The weight ratio of cyclodextrin/antimicrobial agent is usually 0.1/1 to 1/0.05, especially 0.5/1 to 1/0.1. A weight ratio of about 1/1 to 1/0.1 is preferred. After preparation it is preferred that the non-reactive inclusion complex is isolated, for example by filtration, or the reaction mixture obtained according to step a) is used as such. Preferably, the product obtained is not dried before carrying out step b). This means that the wet cake obtained after filtration is used as such for step b) or, alternatively, the reaction mixture obtained according to step a) is used directly for step b).

Step b) is usually carried out at temperatures of 0 to 40° C., especially 0 to 25° C., in an aqueous medium containing the non-reactive inclusion complex obtained according to step a) and the fiber-reactive group. The weight ratio of non-reactive inclusion complex/fiber-reactive group is usually 0.1/1 to 1/0.05, especially 0.5/1 to 1/0.1, more preferably 1/1 to 1/0.1.

After preparation of the fiber-reactive inclusion complex the product can be dried, preferably under mild conditions in order to minimise hydrolisation of the fiber-reactive group. Such drying can, for example, be carried out by evaporation at low pressure (like 0.01 to 0.9 bar, especially 0.01 to 0.2 bar), or in a paddle drier or in a spray tower. The temperatures to be used for the drying step can vary depending on the drying method used. For evaporation or drying in a paddle drier temperatures like 20 to 80° C. are preferred. Drying in a spray tower can, for example, be carried out at temperatures of 100 to 200° C.

The application of the inclusion complex, as a rule, is carried out in aqueous medium. The concentration of the inclusion complex in the aqueous bath is preferably 0.1 to 100 g per liter, especially 2 to 100 g/liter. Highly preferred is a concentration of 2 to 50 g/liter, especially 2 to 25 g/liter. It is preferred to carry out the application of the inclusion complex at a pH of from 4 to 7.

The application can be carried out according to well-known textile related processes; for example according to conventional padding processes. For example, the fiber material is passed through an aqueous liquor containing the inclusion complex, the textile material is squeezed to a defined liquor pick-up rate and then, if desired, a heat treatment can be carried out. The liquor pick-up rate is usually 40% to 200% by weight, especially 50% to 150% by weight, based on the weight of the fiber material.

The heat treatment can be carried out at a temperature of 60 to 200° C., especially 90 to 200° C. Preferred is a temperature of 150 to 200° C. Prior to the heat treatment, it is preferred to dry the fiber materials.

The padding process is usually carried out as a continuous process wherein the fiber material is continuously passed through the aqueous liquor containing the inclusion complex.

Furthermore, the application can also be carried out according to known exhaustion processes. According to this process the fiber materials are immersed into a bath. The temperature to be used can vary between 20 to 100° C.

Fiber materials which can be treated with the inclusion complex are fiber materials comprising, for example, natural or synthetic polyamide (like wool, silk, nylon) and cellulose-containing textile materials of all kinds, for example regenerated or especially natural cellulose fibres, such as cotton, linen, jute, hemp, ramie and polyester; or blends containing the above fiber materials, like polyamide/polyester, polyester/cotton and polyester/wool.

Preferred fiber materials are those comprising wool, synthetic polyamide and especially cellulose-containing fiber materials, preferably cotton.

The fiber material can be in different forms of presentation, as woven or knitted fabrics or as piece goods such as knitgoods, nonwoven textiles, carpets, yarn or staple fibres.

Furthermore, the present invention is directed to aqueous compositions comprising the above inclusion complexes. As to these compositions the above meanings and preferences apply.

Another object of the present invention are the inclusion complexes given above. As to these inclusion complexes the above meanings and preferences apply.

In the following Examples, percentages are by weight.

EXAMPLE 1

Preparation of the Inclusion Complex 38.5 g of Cavasol W7 MCT® (β-cyclodextrin which contains 2 to 3 fiber-reactive monochlorotriazinyl groups which are substituted by —ONa and are attached to the cyclodextrin via a bridge member of formula —O—; commercially available from Wacker Chemie AG, Germany) and 33.5 g of deionised water are mixed to form Mixture A).

7.5 g of the antimicrobial agent of formula

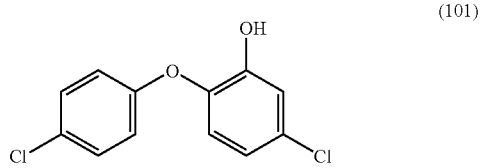

(101)

and 7.5 g of ethanol are mixed to form Mixture B).

Mixture A) is transferred to a Kenwood-kneader and Mixture B) is added in portions during kneading. After all of Mixture B) has been added kneading is continued for 4 hours. The resulting product is put into a dryer and the solvent is evaporated at a temperature of 60° C. Finally, the product is ground in a mortar.

EXAMPLE 2

Application of the Inclusion Complex Prepared According to Example 1 a) Preparation of the Formulation of the Inclusion Complex 10.03 g of the inclusion complex prepared according to Example 1 are dissolved in 500 ml water and acidified by addition of about 8 ml acetic acid to give a pH of 5.

b) Application of the Formulation Prepared According to a)

The formulation is in each case applied on undyed cotton fabric by padding with a pick-up rate of 100%. The pressure is adjusted to a pick-up rate of 100% (1.8 bar). Then the samples indicated in column 1 of the following Table 1 were treated as follows:

Sample 1: dried at room temperature/unwashed (Reference)
Sample 2: first dried at room temperature and then 5 minutes at 150° C./unwashed
Sample 3: first dried at room temperature and then 5 minutes at 170° C./unwashed
Sample 4: dried at room temperature/20× washed (Reference)
Sample 5: first dried at room temperature and then 5 minutes at 150° C./20× washed
Sample 6: first dried at room temperature and then 5 minutes at 170° C./20× washed
Sample 7: dried at room temperature/30× washed (Reference)
Sample 8: first dried at room temperature and then 5 minutes at 150° C./30× washed
Sample 9: first dried at room temperature and then 5 minutes at 170° C./30× washed c) Washing Test The fabric is washed 20 times (or 30 times, respectively) under the following washing conditions:
Detergent: 30 g IEC 456-A (standard detergent)
Washing machine: Wascator FOM 71MP LAB
Temperature: 40° C.

d) Antimicrobial Tests (Determination of the Antimicrobial Efficacy of the Treated Fibre)

The antibacterial activity of a sample has been tested in an agar diffusion test.

| | |
|---|---|
| Microbiological evaluation: | Determination of the bacteriostatic activity according to the bacterial growth inhibition test. |
| Principle: | Discs of the treated cotton samples with 20 mm diameter are cut under sterile conditions and then applied on the top layer of the solidified agar containing the bacteria (from over-night cultures, an 1:500 (*S. aureus*) and an 1:1000 (*E. coli*) dilution is made and 3.5 ml are added to 500 ml of molten agar). After the incubation, the inhibition zones are measured and the results obtained are set out in Table 1. |
| Test bacteria | *Staphylococcus aureus* ATCC 9144 *Escherichia coli* NCTC 8196 |
| Nutrient medium: | Casein soy meal pepton agar (two layers of agar: 15 ml bottom layer without germs and 6 ml top layer with bacteria) |
| Incubation: | 18–24 hours at 37° C. |

TABLE 1

(All tests were performed twice and both results are given in the table)

| Cotton samples and treatment of the samples after application of the formulation | Staph. aureus ZI | Escherichia coli ZI |
|---|---|---|
| 1: dried at RT/unwashed (Reference) | 28/28 | 21/22 |
| 2: dried at RT + 5 minutes at 150° C./unwashed | 26/27 | 19/19 |
| 3: dried at RT + 5 minutes at 170° C./unwashed | 26/27 | 20/21 |
| 4: dried at RT/washed 20 times (Reference) | 4/5 | 3/3 |
| 5: dried at RT + 5 minutes at 150° C./washed 20 times at 40° C. | 10/9 | 7/7 |

TABLE 1-continued (All tests were performed twice and both results are given in the table)

| Cotton samples and treatment of the samples after application of the formulation | Staph. aureus ZI | Escherichia coli ZI |
|---|---|---|
| 6: dried at RT + 5 minutes at 170° C./washed 20 times at 40° C. | 10/10 | 6/7 |
| 7: dried at RT/washed 30 times (Reference) | 4/3 | 1/1 |
| 8: dried at RT + 5 minutes at 150° C./washed 30 times at 40° C. | 7/8 | 4/5 |
| 9: dried at RT + 5 minutes at 170° C./washed 30 times at 40° C. | 10/10 | 6/6 |

Legend:
RT = room temperature
ZI = zone of inhibition in mm around the disc

EXAMPLE 3

Preparation of the Inclusion Complex 38.4 g of Cavasol W7 MCT® (commercially available from Wacker Chemie AG, Germany) and 33.5 of water are mixed together to form Mixture A.

7.5 g of the antimicrobial agent of formula

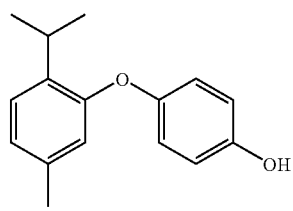
(102)

and 7.5 g ethanol are mixed together to form Mixture B.

Mixture A is transferred to a Kenwood-kneader and Mixture B is added in portions during kneading. After complete addition of Mixture B the kneading process is continued for about 4 hours. Then the paste is put in a (vacuum) dryer at about 60° C. in order to evaporate the solvent and the water. Finally the dried product is ground in a mortar in order to obtain a flowable powder.

EXAMPLE 4

Preparation of the Inclusion Complex 24 g of Cavasol W7 MCT® (commercially available from Wacker Chemie AG, Germany) are added to 70 g of water under stirring. Stirring is continued for one hour to form a solution. Then the pH is adjusted to a value of 7.5 by addition of 2.5 g of disodium hydrogen phosphate. 4 g of the antimicrobial agent of formula (101) are added under stirring and stirring is continued for 16 hours at a temperature of 40° C. Then the solution having a turbid appearance is filtered by suction and the resulting clear solution is dried at a pressure of 50 mbar and a temperature of about 40° C. in a paddel drier (Venuleft). Obtained are 28 g of a white product which can be applied to cotton fabric according to the procedure given in Example 2.

EXAMPLE 5

Preparation of the Inclusion Complex 24 g of Cavasol W7 MCT® (commercially available from Wacker Chemie AG, Germany) are added to 70 g of water under stirring. A small amount of a defoaming agent is added and stirring is continued for one hour to form a solution. Then the pH is adjusted to a value of 7.5 by addition of 2.5 g of disodium hydrogen phosphate. 4.5 g of the antimicrobial agent of formula

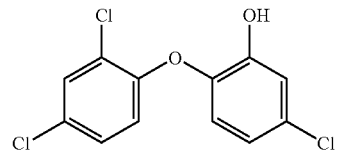
(103)

are added under stirring and stirring is continued for 10 hours at a temperature of 40° C. Then the solution having a turbid appearance is passed over a filter press and the resulting clear solution is dried in a spray dryer at an inlet temperature of 180° C. Obtained are 29 g of a white product which can be applied to cotton fabric according to the procedure given in Example 2.

EXAMPLE 6

Preparation of the Inclusion Complex 24 g of Cavasol W7 MCT® (commercially available from Wacker Chemie AG, Germany) are added to 70 g of water under stirring. Stirring is continued for one hour to form a solution. Then the pH is adjusted to a value of 10 by addition of the appropriate amount of sodium hydroxide. 4 g of the antimicrobial agent of formula (101) are added under stirring and stirring is continued for 16 hours at a temperature of 40° C. The pH is kept at a value of 10 by addition of sodium hydroxide. Then the solution having a turbid appearance is filtered by suction and the resulting clear solution is dried at a pressure of 50 mbar and a temperature of about 40° C. in a paddel drier (Venulett). Obtained are 28 g of a white product which can be applied to cotton fabric according to the procedure given in Example 2.

EXAMPLE 7

Preparation of the Inclusion Complex a) 31 g of β-cyclodextrin are added to 1000 g of deionised water at a temperature of 60° C. under stirring and stirring is continued for 15 minutes to form a solution. Then 7 g of the antimicrobial agent of formula (101) are added and the solution is stirred at a temperature of 60° C. for two hours. Subsequently the solution is cooled to 20° C. The resulting white suspension is filtered by suction. The wet cake obtained is dissolved in 40 g of water and 9.5 g of a sodium hydroxide solution (36%).

b) A separate solution is prepared by adding 12.4 g of cyanuric chloride and a small amount of a defoaming agent to a mixture of 60 g of water and 60 g of ice. For 5 hours the mixture is held at a temperature of 0 to 5° C. and a pH of 9 to 11 (by addition of a sodium hydroxide solution, 36%).

c) The solution prepared according to a) is added to the solution prepared according to b) within 2 hours, keeping the pH at a value of about 10 to 12. Stirring is continued for 3 hours, the mixture is filtered and the clear solution is subjected to a rotary evaporator at a temperature of about 40° C. and a pressure of 50 mbar. 50 g of a white product are obtained which can be applied to cotton fabric according to the procedure given in Example 2.

EXAMPLE 8

Preparation of the Inclusion Complex a) A separate solution is prepared by addition of 20 g of cyanuric chloride to a mixture of 100 g of water, 90 g of ice and a small amount of a defoaming agent at a temperature of 0 to 5° C. For about 5 hours the mixture is held at a temperature of 0 to 5° C. and a pH of 9 to 12 (by addition of a sodium hydroxide solution, 36%).

b) A further solution is prepared by addition of 30.8 g of β-cyclodextrin to a mixture of 40 g of water and 15.6 g of a sodium hydroxide solution.

c) The solution prepared according to b) is added to the solution prepared according to a) over a period of 3 hours keeping the pH at a value of 10 to 12. Stirring is continued for 3 hours at a pH value of 8 to 10. The mixture is filtered and 14 g of the antimicrobial agent of formula (103) as well as 4.5 g of disodium hydrogen phosphate are added to the clear solution. Stirring is continued for 16 hours at a temperature of 40° C. The resulting solution having a turbid appearance is filtered by suction and the resulting clear solution is dried at a pressure of 50 mbar and a temperature of about 40° C. in a paddel drier (Venulett). Obtained are 60 g of a white product which can be applied to cotton fabric according to the procedure given in Example 2.

We claim:

1. A process for durable antimicrobial treatment of natural or synthetic polyamide or cellulosic fibers, comprising
    reacting an inclusion complex of a fiber-reactive cyclodextrin containing an antimicrobial agent with said fibers, and having fiber reactive groups bonded to the cyclodextrim wherein the antimicrobial agent is selected from the group consisting of
    (a) halogeno-o-hydroxydiphenyl compounds of the formula

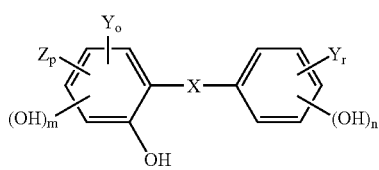

(1)

wherein
X is oxygen, sulfur or —$CH_2$—,
Y is chloro or bromo,
Z is $SO_2H$, $NO_2$ or $C_1$–$C_4$-Alkyl,
r is 0 to 3,
o is 0 to 3,
p is 0 or 1,
m is 0 or 1 and
n is 0 or 1;
and at least one of r or o is ≠0, and non-halogenated hydroxydiphenyl ether compounds of the formula

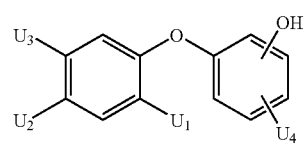

(1')

wherein
$U_1$ and $U_2$ are independently of each other hydrogen, hydroxy, unsubstituted or hydroxy-substituted $C_1$–$C_{20}$alkyl, $C_5$–$C_7$cycloalkyl, $C_1$–$C_6$alkylcarbonyl, $C_1$–$C_{20}$alkoxy, phenyl or phenyl-$C_1$–$C_3$-alkyl;
$U_3$ is hydrogen, $C_1$–$C_{20}$alkyl, $C_1$–$C_{20}$alkoxy or $C_1$–$C_6$alkylcarbonyl; and
$U_4$ is hydrogen, unsubstituted or hydroxy-substituted $C_1$–$C_{20}$alkyl, $C_5$–$C_7$cycloalkyl, hydroxy, formyl, acetonyl, $C_1$–$C_6$alkylcarbonyl, $C_2$–$C_{20}$alkenyl, carboxy, carboxy$C_1$–$C_3$alkyl, $C_1$–$C_3$alkylcarbonyl-$C_1$–$C_3$alkyl or carboxyallyl.

2. A process according to claim 1, wherein the antimicrobial agent (a) is a compound of formula (1), wherein
X is oxygen, sulfur or —$CH_2$—, and
Y is chloro or bromo,
m is 0,
n is 0 or 1,
o is 1 or 2,
r is 1 or 2 and
p is 0.

3. A process according to claim 1, wherein the antimicrobial agent (a) is a compound of formula

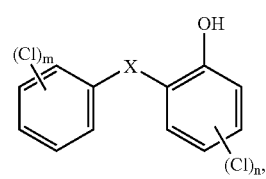

(2)

wherein
X is —O— or —$CH_2$—;
m is 1 to 3; and
n is 1 or 2.

4. A process according to claim 1 wherein the antimicrobial agent (a) is a compound of formula

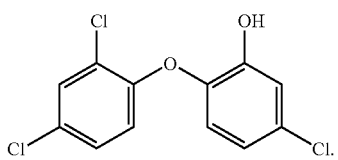

(3)

5. A process according to claim 1 wherein the antimicrobial agent (a) compound of formula

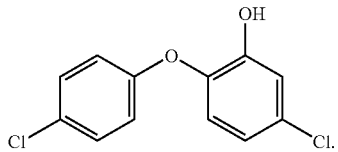
(4)

6. A process according to claim 1 wherein $U_1$ and $U_3$ are $C_1$–$C_4$alkyl and $U_2$ and $U_4$ are hydrogen.

7. A process according to claim 1, wherein the fiber-reactive group of the cyclodextrin is a nitrogen-containing heterocycle having at least one substituent selected from the group consisting of halogen and pyridinium radicals.

8. A process according to claim 1, wherein the fiber-reactive group of the cyclodextrin is a) a triazine group of formula

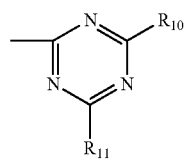
(10)

wherein $R_{10}$ is fluorine, chlorine or unsubstituted or carboxy-substituted pyridinium, and $R_{11}$ is as defined above for $R_{10}$ or is a radical of formula —$OR_{12}$ or —$N(R_{13})R_{14}$, wherein $R_{12}$ is hydrogen, alkali, $C_1$–$C_8$alkyl which is unsubstituted or substituted by hydroxy or $C_1$–$C_4$alkoxy, and $R_{13}$ and $R_{14}$, independently from each other, are hydrogen; $C_1$–$C_8$alkyl which is unsubstituted or substituted by $C_1$–$C_4$alkoxy, hydroxy, sulfo, sulfato or carboxy; or phenyl which is unsubstituted or substituted by $C_1$–$C_4$alkyl, $C_1$–$C_4$alkoxy, halogen, nitro, carboxy or sulfo;

b) or is a pyrimidinyl group of formula

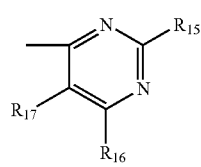
(11)

wherein one of radicals $R_{15}$ and $R_{16}$ is fluorine or chlorine and the other one of radicals $R_{15}$ and $R_{16}$ is fluorine, chlorine, or is a radical of formula —$OR_{12}$ or —$N(R_{13})R_{14}$ as defined above, and $R_{17}$ is $C_1$–$C_4$alkylsulfonyl, $C_1$–$C_4$alkoxysulfonyl, $C_1$–$C_4$alkoxycarbonyl, $C_2$–$C_4$alkanoyl, chlorine, nitro, cyano, carboxyl or hydroxyl;

c) or is a dichloroquinoxaline group of formula

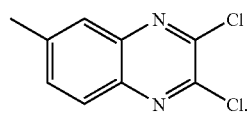
(12)

9. A process according to claim 8, wherein the fiber-reactive group of the cyclodextrin is a triazine group of formula

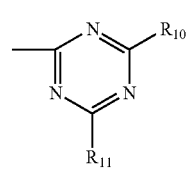
(10)

wherein $R_{10}$ is chlorine, and $R_{11}$ is a radical of formula —$OR_{12}$, wherein $R_{12}$ is hydrogen, an alkali metal or $C_1$–$C_8$alkyl.

10. A process according to claim 1, wherein the cyclodextrin contains 2 to 3 fiber-reactive groups.

11. A process according to claim 1, wherein the application of the inclusion complex is carried out in an aqueous medium containing 2 to 100 g per liter of the inclusion complex.

12. A process according to claim 1, wherein the application of the inclusion complex is carried out at a pH of from 4 to 7.

13. A process according to claim 1, wherein the application of the inclusion complex is carried out by a padding technique.

14. A process according to claim 1, wherein the fiber material, after application of the inclusion complex, is treated at a temperature of 100 to 200° C.

15. An aqueous composition comprising an inclusion complex of a fiber-reactive cyclodextrin having fiber reactive groups bonded to the cyclodextrin and containing an antimicrobial agent, which agent is selected from the group consisting of (a) halogeno-o-hydroxydiphenyl compounds of the formula

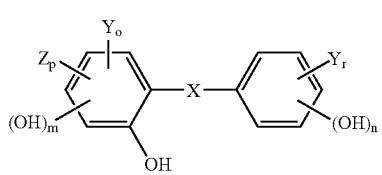
(1)

wherein

X is oxygen, sulfur or —$CH_2$—,

Y is chloro or bromo,

Z is $SO_2H$, $NO_2$ or $C_1$–$C_4$-Alkyl, r is 0 to 3, o is 0 to 3, p is 0 or 1, m is 0 r 1 and n is 0 or 1;
and at least one of r or o is ≠0,
and non-halogenated hydroxydiphenyl ether compounds of the formula

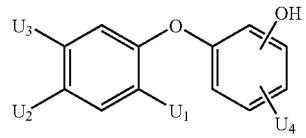

(1')

wherein
$U_1$ and $U_2$ are independently of each other hydrogen, hydroxy, unsubstituted or hydroxy-substituted $C_1$–$C_{20}$alkyl, $C_5$–$C_7$cycloalkyl, $C_1$–$C_8$alkylcarbonyl, $C_1$–$C_{20}$alkoxy, phenyl or phenyl-$C_1$–$C_3$-alkyl;
$U_3$ is hydrogen, $C_1$–$C_{20}$alkyl, $C_1$–$C_{20}$alkoxy or $C_1$–$C_6$alkylcarbonyl; and
$U_4$ is hydrogen, unsubstituted or hydroxy-substituted $C_1$–$C_{20}$alkyl, $C_5$–$C_7$cycloalkyl, hydroxy, formyl, acetonyl, $C_1$–$C_6$alkylcarbonyl, $C_2$–$C_{20}$alkenyl, carboxy, carboxy$C_1$–$C_3$alkyl, $C_1$–$C_3$alkylcarbonyl-$C_1$–$C_3$alkyl or carboxyallyl.

16. An inclusion complex of a fiber-reactive cyclodextrin having fiber reactive group bonded to the cyclodextrin and containing an antimicrobial agent, which agent is selected from the group consisting of
(a) halogeno-o-hydroxydiphenyl compounds of the formula

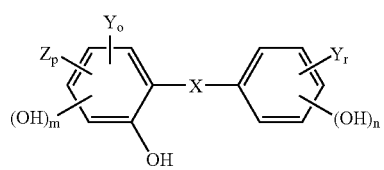

(1)

wherein
X is oxygen, sulfur or —CH$_2$—,
Y is chloro or bromo,
Z is SO$_2$H, NO$_2$ or $C_1$–$C_4$-Alkyl,
r is 0 to 3,
o is 0 to 3,
p is 0 or 1,
m is 0 or 1 and n is 0 or 1;
and at least one of r or o is ≠0,
and non-halogenated hydroxydiphenyl ether compounds of the formula

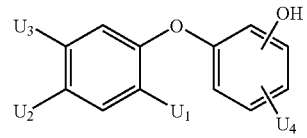

(1')

wherein
$U_1$ and $U_2$ are independently of each other hydrogen, hydroxy, unsubstituted or hydroxy-substituted $C_1$–$C_{20}$alkyl, $C_5$–$C_7$cycloalkyl, $C_1$–$C_8$alkylcarbonyl, $C_1$–$C_{20}$alkoxy, phenyl or phenyl-$C_1$–$C_3$-alkyl;
$U_3$ is hydrogen, $C_1$–$C_{20}$alkyl, $C_1$–$C_{20}$alkoxy or $C_1$–$C_8$alkylcarbonyl; and
$U_4$ is hydrogen, unsubstituted or hydroxy-substituted $C_1$–$C_{20}$alkyl, $C_5$–$C_7$cycloalkyl, hydroxy, formyl, acetonyl, $C_1$–$C_8$alkylcarbonyl, $C_2$–$C_{20}$alkenyl, carboxy, carboxy$C_1$–$C_3$alkyl, $C_1$–$C_3$alkylcarbonyl-$C_1$–$C_3$alkyl or carboxyallyl.

17. A process for the preparation of a fiber-reactive inclusion complex as defined in claim 16, which comprises forming an inclusion complex of a fiber-reactive cyclodextrin with at least one antimicrobial agent as defined in claim 16 at a pH of ≧9.

18. A process for the preparation of a fiber-reactive inclusion complex as defined in claim 16, which comprises the steps of
a) forming an inclusion complex of a cyclodextrin which contains at least one antimicrobial agent as defined in claim 16; and then
b) introducing at least one fiber-reactive group into the cyclodextrin in the inclusion complex obtained according to step a).

19. A process according to claim 18 wherein the inclusion complex obtained according to step a) is processed directly without intermediate drying.

20. A process according to claim 1, wherein the cellulosic fiber is cotton.

21. A process according to claim 1, wherein the fibers are in the form of a woven or knitted fabric, a nonwoven textile, a carpet, yarn or staple fiber.

* * * * *